United States Patent
Wang

(10) Patent No.: US 7,623,946 B2
(45) Date of Patent: Nov. 24, 2009

(54) SYSTEM AND METHOD THAT WILL SYNCHRONIZE DATA ACQUISITION AND MODULATION IN A COMPREHENSIVE TWO (MULTI) DIMENSIONAL CHROMATOGRAPHY (SEPARATION) SYSTEM TO ENABLE QUANTITATIVE DATA ANALYSIS

(75) Inventor: Frank C. Wang, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/492,358

(22) Filed: Jul. 25, 2006

(65) Prior Publication Data

US 2007/0071650 A1    Mar. 29, 2007

Related U.S. Application Data

(60) Provisional application No. 60/708,612, filed on Sep. 12, 2005.

(51) Int. Cl.
   *G05B 21/00*    (2006.01)
   *G01N 30/30*    (2006.01)

(52) U.S. Cl. .................. 700/266; 700/271; 700/273; 436/161; 422/89; 702/22; 702/23

(58) Field of Classification Search .............. 422/89; 436/161; 700/266, 271, 273; 702/22–23
See application file for complete search history.

(56) References Cited

U.S. PATENT DOCUMENTS

| | | | | |
|---|---|---|---|---|
| 3,751,966 | A * | 8/1973 | Ryan et al. | 73/23.36 |
| 4,869,093 | A * | 9/1989 | Gilbert | 73/23.35 |
| 5,116,764 | A * | 5/1992 | Annino et al. | 436/161 |
| 5,612,225 | A * | 3/1997 | Baccanti et al. | 436/114 |
| 6,311,544 | B1 * | 11/2001 | Bertrand | 73/23.35 |
| 6,494,078 | B1 * | 12/2002 | Klee | 73/23.35 |
| 6,702,989 | B2 * | 3/2004 | Sacks et al. | 422/89 |
| 6,706,534 | B2 * | 3/2004 | Sacks et al. | 436/161 |
| 6,706,535 | B2 * | 3/2004 | Sacks et al. | 436/161 |
| 6,838,288 | B2 * | 1/2005 | Beens | 436/161 |
| 7,091,044 | B2 * | 8/2006 | Cai et al. | 436/161 |
| 2006/0099716 | A1 * | 5/2006 | Tipler et al. | 436/161 |

FOREIGN PATENT DOCUMENTS

| | | |
|---|---|---|
| EP | 0 000 310 A1 | 1/1979 |
| JP | 01 265157 A | 10/1989 |
| WO | WO 92/13622 | 1/1992 |
| WO | WO 02/39106 A1 | 5/2002 |
| WO | WO 03/067250 A1 | 8/2003 |

OTHER PUBLICATIONS

Schoenmakers, Peter J., et al.: "Comparison of comprehensive two-dimensional gas chromatography and gas chromatography—mass spectrometry for the characterization of complex hydrocarbon mixtures" Journal of Chromatography, Elsevier Science Publishers B.V. Amsterdam, NL, vol. 892, No. 1-2, Sep. 15, 2000, pp. 29-46.

* cited by examiner

*Primary Examiner*—Brian R. Gordon

(57) ABSTRACT

The present invention is a comprehensive two-dimensional gas chromatograph system and method including a modulator wherein the pulsing of the modulator is synchronized with data acquisition so that the results are reproducible.

4 Claims, 7 Drawing Sheets

SYSTEM AND METHOD THAT WILL SYNCHRONIZE DATA ACQUISITION AND MODULATION IN A COMPREHENSIVE TWO (MULTI) DIMENSIONAL CHROMATOGRAPHY (SEPARATION) SYSTEM TO ENABLE QUANTITATIVE DATA ANALYSIS

This application claims the benefit of U.S. Provisional application 60/708,612 filed Sep. 12, 2005.

BACKGROUND OF THE INVETNION

The present invention relates to comprehensive two-dimensional gas chromatography (2DGC or GCxGC). In particular, the invention relates to 2DGC or GCxGC that achieves a reproducible chromatogram.

Two-dimensional gas chromatography is the result of combining two separation columns in gas chromatography. The effluent from the first column is periodically injected/transferred into the second column which separates the components of the effluent by a different criteria than that of the first column. Peak crowding/overlapping limits the usefulness of traditional chromatography. One way of handling the problem of peak crowding is overlapping comprehensive two-dimensional gas chromatography. In this set-up, the effluent from the first column is injected into the second column in a series of pulses by a modulator located between the columns. The modulator periodically stops and starts the movement of the effluent from the first column into the second column. The effluent from the second column is fed to a detector for data acquisition of the constituents of the effluent.

SUMMARY OF THE INVENTION

Comprehensive two dimensional gas chromatographic separation is based on a modulation system to define the start and end of the second dimension separation. The second dimensional separation can be defined by the modulation period of the modulator that gated the effluent flow between the first dimensional and the second dimensional separation. The modulation unit is operated independently of GC data acquisition in the traditional Comprehensive two-dimensional gas chromatography (2DGC or GCxGC) system. This causes (1) the starting time of the second dimensional separation independent of the starting time of first dimensional separation that varies from run to run even if experiment conditions are exactly the same; (2) the peak fractions that are sliced into the second dimension separation are not exactly the same shape/intensity which will create many post data processing problems.

Therefore, "data acquisition synchronization with the modulation" is required for any comprehensive two-dimensional chromatographic type separation in order that the results be reproducible.

In the present invention, a system and method of a synchronization unit have been disclosed to enable accurate time resolution of the GCxGC system. The retention position for any component in the GCxGC chromatograms can be exactly re-produced by GCxGC instrument with this set-up. That is, the data acquisition can be synchronized with the modulator to achieve a reproducible chromatogram. The term "exactly reproduce" is the most important factor for the quantitative analysis of components that separate out by this two-dimensional chromatographic separation.

DETAILED DESCRIPTION OF THE PREFERRED EMBODIMENTS

Comprehensive two-dimensional gas chromatography (GCxGC) has demonstrated that two-dimensional separation can be applied to complex mixtures. There are two major advantages of GCxGC technique when compared to single dimensional GC: increased resolution that is approximately 10 times greater and sensitivity higher by approximately 50 times. In order to implement this new powerful separation instrument as a routine analytical tool, it is very important to automate the multi-steps for unattended operation. In addition, because of its increased resolving power, the interface of GCxGC to such elemental selective detectors as sulfur is very important in solving complex composition problems.

The present invention is an improved comprehensive two-dimensional gas chromatography that is automated, that is, allows unattended operation. In addition to the unattended operation of the instrument, the chromatogram can now be reproduced with greater precision which allows improved control of the quantitative analysis step.

Figure 1:
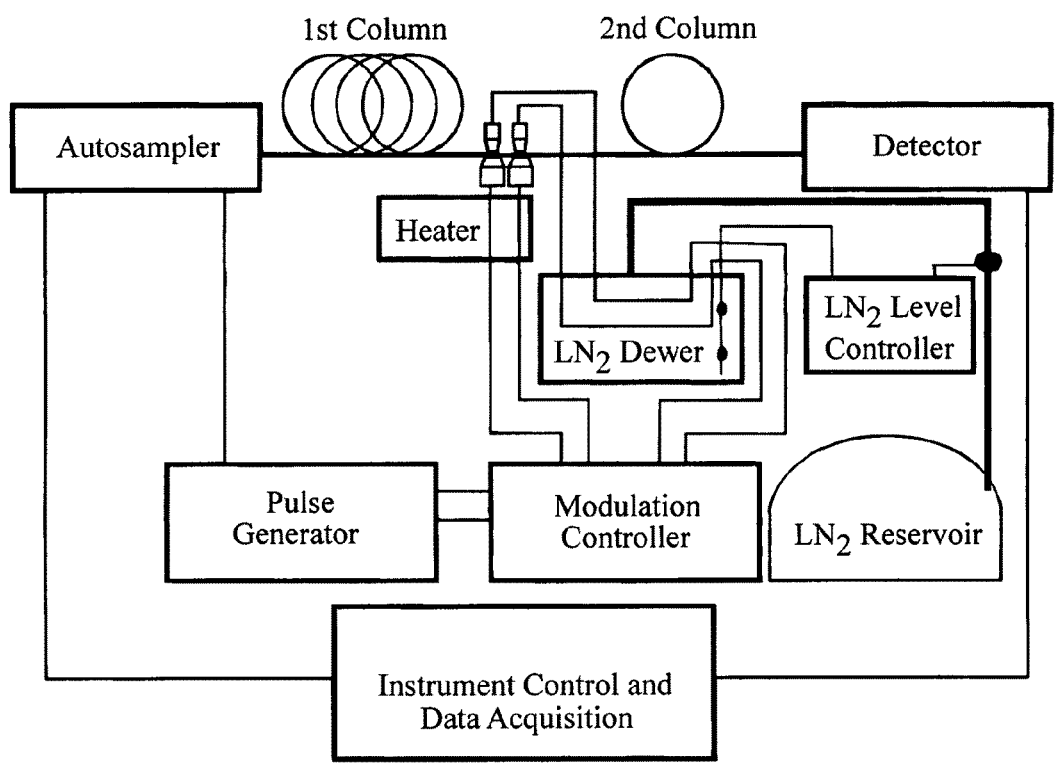
FIG. 1 shows a schematic drawing of the GCxGC unit of the present invention.

The GCxGC schematic in FIG. 1 illustrates the functional diagram of the different units and their role in the automatic operation. This automation development include: (1) the use of liquid nitrogen level control and automatic liquid nitrogen refill system; (2) addition of an autosampler; (3) improved instrument control and data acquisition software; and (4) introduced pulse generator with external trigging option to synchronize the modulation with GC event.

The role of liquid nitrogen is to perform a heat exchange of nitrogen gas to provide the cool gas source for the cold jet during the solute trapping phase of the modulation. This is required in order to trap the solute coming out from the first dimensional column. A continuous supply of the liquid nitrogen is needed in order to operate the modulation unit over the required many cycles to complete an analysis. A liquid nitrogen level control system in addition to a liquid nitrogen refill kit have been introduced as part of the automation package.

For the automation of GCxGC for multi-sample analysis, the first requirement is an autosampler. The autosampler from the same GC manufacturer was chosen because it closely meets all of the requirements.

The original commercial GCxGC system included a software program to control the modulation unit and data acquisition. However, this program was not capable of performing automated data acquisition. A separate commercially available data acquisition program had to be used and adapted into this GCxGC operation. The new program was able to integrate with other operation units such as the autosampler and pulse generator, resulting in a fully automated system.

In the prior art GCxGC system design, the modulation unit was operated independently of the GC data acquisition. The result of this independence caused a phase shift in the second dimensional chromatogram, resulting in non-reproducible chromatograms. In order to correct this, either phase correction software or hardware synchronization was necessary. This development concentrated on the hardware synchronization solution to achieve a reproducible chromatogram.

In the present invention, data acquisition was synchronized with modulation, resulting in a fully automatic operation. The performance enhancement attained with the synchronization and is demonstrated with several applications of GCxGC in the analysis of complex mixtures. Two typical applications include: 1) the separation of diesel boiling point range fuels to show the power of class type separation to distinguish various fuels and 2) GCxGC sulfur specific detection of sulfur containing compounds in diesel range streams during different stages of hydrodesulfuration (HDS) process to demonstrate the power of class type separation of hard sulfur compounds as well as the HDS catalytic selectivity and efficiency.

The Automation of GCXGC

The GCxGC unit was purchased from Zoex Inc. (Lincoln, Nebr.) (There are others available). It employs a GC (Agilent 6890) system, a first generation thermal modulation unit with its controller, and a computer loaded with Zoex's instrument control and data acquisition software. The thermal modulation was accomplished through the use of a rotating slotted heater. The slotted heater did not provide efficient control of the solute trapping during modulation as it was difficult to refocus the solute on a short thicker film coated capillary tube located between the first and second dimension columns. The short capillary tube tracked the oven temperature and was not sufficiently cool to refocus the solute eluting from the first dimension column. As a result, the thermal modulation unit was upgraded to a pulsed jet system. During the modulation upgrading several steps outlined below were taken to completely automate the GCxGC system.

Liquid Nitrogen Level Control and Automatic Liquid Nitrogen Refill System

In order to perform the trapping function of the modulation operation, the nitrogen gas needs to be cooled from room temperature to a subfreezing temperature. In the pulsed jet modulation unit, the source of cold jet (gas) is from an external nitrogen gas supply. The mechanism of this heat exchange is accomplished by passing nitrogen gas through a coil, immersed in liquid nitrogen Dewar flask. The role of liquid nitrogen is to perform the heat exchange of room temperature nitrogen gas to a subfreezing temperature.

Due to the fixed volume of the liquid nitrogen Dewar flask and the need for uninterrupted cooled nitrogen gas, a larger reservoir of liquid nitrogen is needed. This, coupled with automatic filling capability, allows for around the clock operation.

Not only is the re-filling of the liquid nitrogen Dewar important in the automatic mode, but the level of liquid nitrogen is of equal importance. The distance of the level sensors controls the frequency of the re-fill operation. The absolute height of the start sensor will determine the lowest temperature of the cold jet. This liquid nitrogen supply operation can be completely independent from the other required operations of automation. This independence provides the flexibility of selection of liquid nitrogen level control and refill system. Systems employing resistance or capacitance should be able to fulfill the requirement. Our system uses resistance sensors as are well-known in the art.

The Autosampler

The introduction of an autosampler is another important step in the automation for the analysis of multi-samples around the clock. Since some of the GCxGC applications require long analysis times, the use of an autosampler is extremely important. In addition, because of its automated mechanical operation, the timing of injection, the quantity of sample being injected, the speed of injection, and the depth of injection can all be controlled in an accurate and reproducible fashion. All needle effects, such as sample evaporation, due to the needle warm up and sample discrimination due to needle dwell time can all be eliminated. The other important advantage of using an autosampler in the GCxGC is the GC start timing control. The GC start time is a very important time event, which also defines the reference time point of data acquisition as well as the modulation start time. In a GCxGC analysis, the data acquisition has to synchronize with the modulation period. It is very important to be able to control or reference the GC start time in order to use it as a reference point to control/define other events that need to be synchronized.

The autosampler used in GCxGC is exactly the same as the conventional GC autosampler.

The Instrument Control and Data Acquisition Software

In the automation development of the present invention, it is desirable that the software package integrate all hardware components as well as software programs to perform automatic GCxGC experiments.

GCxGC automation requires the control and communication of several different components in the system: 1) the modulation unit, it involves hard and cold jet flow, heating of the hot jet, and cooling of the cold jet. The gas valves need to be turned on and off before and after the analysis. The electric power of the heater and the power of liquid nitrogen level control and re-fill system are also needed to be turned on and off before and after the analysis; 2) the GCxGC instrument control which includes method set-up, sequence set-up, the autosampler control, as well as the data acquisition; this portion is the same as in traditional GC; 3) the synchronization with the external timing device such as a pulse generator; 4) the control of the heating and cooling in the secondary oven chamber; 5) be able to perform a high-speed sampling in order to meet the requirement of GCxGC sample rate.

If one software package can control all of the events required to perform an experiment, then, all the required parameters can be compiled into a command file and be repeated many times. This command file is called the method file in the software package used in this automation development. During a run sequence, different method files can be called to perform different tasks. This is the advantage of data acquisition software, as well as the truly automation of this instrumentation.

There are many commercially available GC instrument control and data acquisition packages. The software package used in this automation is the one from the same vendor of the GC and autosampler. However, this package does not synchronize the modulation unit with GC data acquisition.

The Synchronization System

In the original GCxGC system, the modulation unit is operated independently of GC data acquisition. This causes the peak position to vary in the second dimension of the GCxGC chromatogram. Chromatograms will not be the same in the second dimension position even if they are run in exactly by the same experimental conditions. The result is that the data acquisition is not synchronized with the pulses in the modulation unit.

In order to have the same retention time in the second dimensional column; the data acquisition start has to be synchronized with a reference time point of modulation unit. In the present invention, the way to achieve this is to have the data acquisition starting point synchronize with the pulse sequence starting point. Because the pulse sequence starts much earlier than the GC data acquisition starts, it is necessary to reset the pulse sequence when data acquisition starts.

Figure 2:
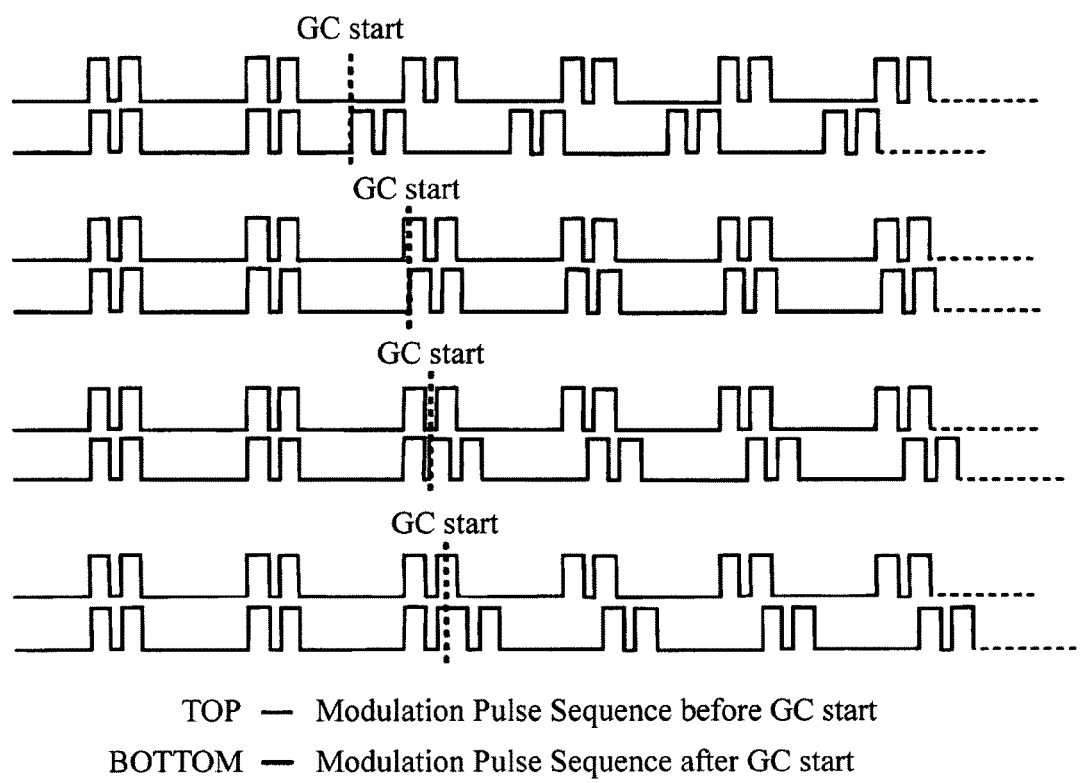
FIG. 2 shows how the interrupt and reset pulse sequence synchronizes the GC start with data acquisition.

Synchronization can also be achieved by post-analysis software correction. However, this will require either a reference component spike in the sample or an instrumentally created reference signal. Post-analysis software correction also requires additional steps to attain a scientifically meaningful chromatogram. The hardware synchronization approach will generate the correct chromatogram every time with no further manipulation required. In this automation development, a pulse generator is introduced with the option of external triggering. When the GC is ready to start, this is the same time data acquisition is ready to start, the autosampler sends out a triggering signal to the pulse generator unit to reset the pulse sequence. This trigging mechanism enables the pulse generator to synchronize with the data acquisition start point. FIG. 2 illustrates how this interrupt and reset pulse sequence synchronizes the GC start with data acquisition.

Performance of Synchronized GCXGC

Test of Synchronization

In conventional GC analysis, if the identification of a component is based on the retention time, the variation of retention time between different runs cannot be more than three data points. Depending on the sampling frequency, these three data points may require the retention time difference to be no more than ±0.02 minute if the data is collected at 1 hertz (Hz) rate. In the GCxGC, under the same conditions, the variation of the retention time cannot be more than ±0.001 minute. This is because the sampling rate is typically 100 Hz in the GCxGC. In order to have the retention time position for the same compound, it is necessary to synchronize the modulation process with the data acquisition. The following examples demonstrate the retention time variation of a group of compounds in the chromatograms that were obtained with and without the synchronization between modulation process and data acquisition.

In conventional GC analysis, if the identification of a component is based on the retention time, the variation of retention time between different runs cannot be more than three data points. Depending on the sampling frequency, these three data points may require the retention time difference to be no more than ±0.02 minute if the data is collected at 1 hertz (Hz) rate. In the GCxGC, under the same conditions, the variation of the retention time cannot be more than ±0.001 minute. This is because the sampling rate is typically 100 Hz in the GCxGC. In order to have the same retention time (retention position for GCxGC) for the same compound, it is necessary to synchronize the modulation process with the data acquisition. The following examples demonstrate the retention time variation of a group of compounds in the chromatograms that were obtained with and without the synchronization between modulation process and data acquisition.

Table 1 shows the retention time of C13-C16 paraffins with the modulation process synchronized with data acquisition. After four different runs, the variation of retention time within the corresponding peaks is less than ±0.001 minute. This ensures that every compound will reappear at the same position all the times in the GCxGC chromatograms.

TABLE 1

The Retention time of C13 to C16 normal paraffin standard within different runs with modulation synchronized with data acquisition.

| | Runs | | | | | |
| --- | --- | --- | --- | --- | --- | --- |
| | 1 Retention Time | 2 Retention Time | 3 Retention Time | 4 Retention Time | Average | Stdev |
| C13 | 23.391 | 23.391 | 23.391 | 23.391 | 23.391 | <0.001 |
| | 23.559 | 23.559 | 23.559 | 23.559 | 23.559 | <0.001 |
| | 23.723 | 23.723 | 23.723 | 23.723 | 23.723 | <0.001 |
| C14 | 27.892 | 27.892 | 27.892 | 27.892 | 27.892 | <0.001 |
| | 28.061 | 28.061 | 28.061 | 28.061 | 28.061 | <0.001 |
| | 28.226 | 28.226 | 28.226 | 28.226 | 28.226 | <0.001 |
| C15 | 32.228 | 32.228 | 32.228 | 32.228 | 32.228 | <0.001 |
| | 32.396 | 32.396 | 32.396 | 32.396 | 32.396 | <0.001 |
| | 32.561 | 32.561 | 32.561 | 32.561 | 32.561 | <0.001 |
| C16 | 36.369 | 36.369 | 36.369 | 36.369 | 36.369 | <0.001 |
| | 36.656 | 36.656 | 36.656 | 36.656 | 36.656 | <0.001 |
| | 36.729 | 36.729 | 36.729 | 36.729 | 36.729 | <0.001 |

Figure 3:
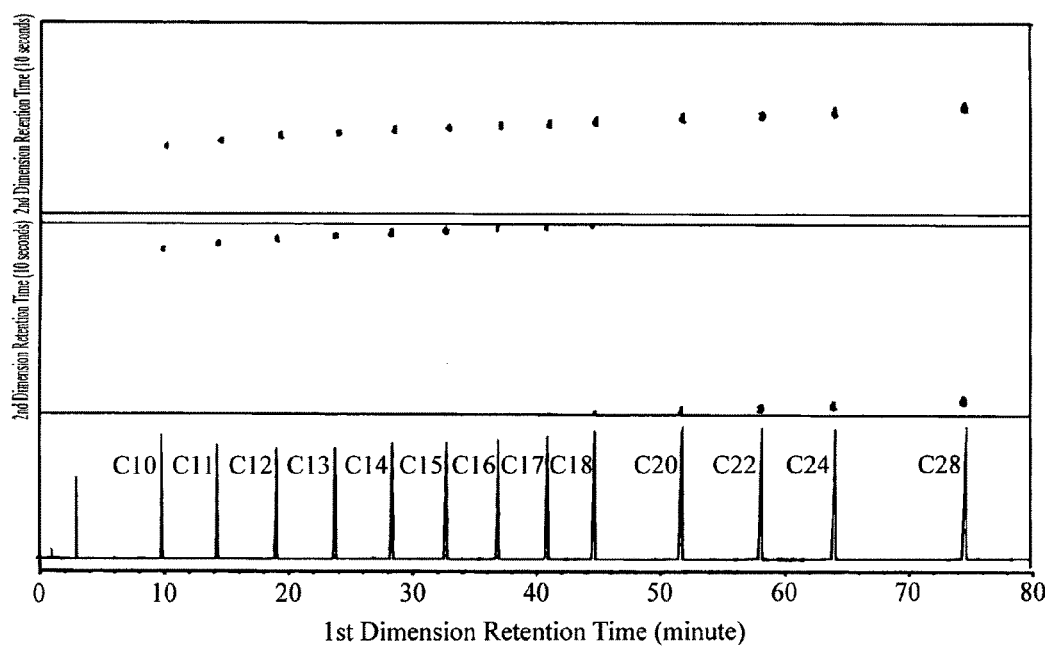
FIG. 3 shows that for the data of Table 2 the modulation process is not synchronized with data acquisition, the variation of the retention time will make the same compound appear not in the same position (in the second dimension) in the GCxGC chromatogram.

Table 2 shows another set of retention time of C13-C16 paraffins with the modulation process not synchronized with data acquisition. After four different runs, the variation of retention time in the peaks is approximately ±0.167 minute (10-seconds/modulation period). Because of the modulation process is not synchronized with data acquisition, the variation of the retention time will make the same compound appear not in the same position (in the second dimension) in the GCxGC chromatogram, which can be viewed in the FIG. 3.

TABLE 2

The Retention time of C13 to C16 normal paraffin standard within different runs with modulation not synchronized with data acquisition.

| | Runs | | | | | |
| --- | --- | --- | --- | --- | --- | --- |
| | 1 Retention Time | 2 Retention Time | 3 Retention Time | 4 Retention Time | Average | Stdev |
| C13 | 23.391 | 23.426 | 23.414 | 23.330 | 23.390 | 0.043 |
| | 23.559 | 23.630 | 23.583 | 23.498 | 23.568 | 0.055 |
| | 23.723 | | 23.746 | 23.664 | 23.711 | 0.042 |
| C14 | 27.892 | 27.964 | 27.917 | 27.832 | 27.901 | 0.055 |
| | 28.061 | 28.132 | 28.086 | 27.999 | 28.070 | 0.055 |
| | 28.226 | 28.295 | 28.250 | 28.167 | 28.235 | 0.053 |
| C15 | 32.228 | 32.299 | 32.251 | 32.167 | 32.236 | 0.055 |
| | 32.396 | 32.468 | 32.421 | 32.334 | 32.405 | 0.056 |
| | 32.561 | 32.630 | 32.585 | 32.503 | 32.570 | 0.053 |

TABLE 2-continued

The Retention time of C13 to C16 normal paraffin standard within different runs with modulation not synchronized with data acquisition.

|   | Runs | | | | | |
|---|---|---|---|---|---|---|
|   | 1 Retention Time | 2 Retention Time | 3 Retention Time | 4 Retention Time | Average | Stdev |
| C16 | 36.369 | 36.467 | 36.420 | 36.335 | 36.398 | 0.058 |
|  | 36.656 | 36.636 | 36.589 | 36.504 | 36.596 | 0.068 |
|  | 36.729 | 36.802 | 36.752 | 36.670 | 36.738 | 0.055 |

Figure 4:
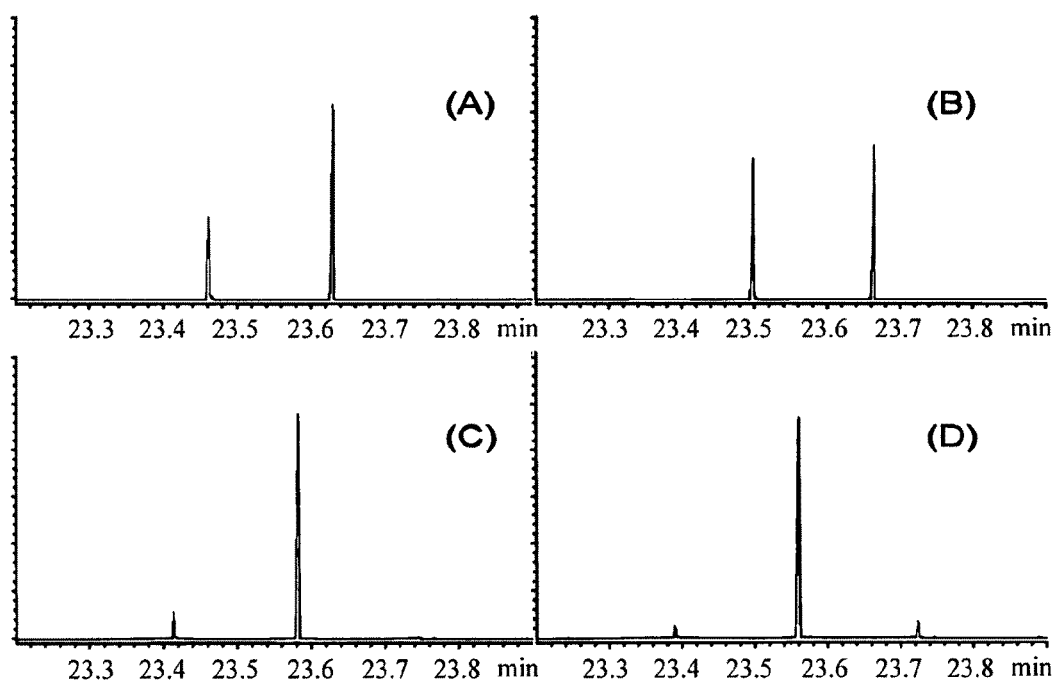
FIG. 4 shows the peak pattern of the C13-C16 normal paraffin standard for four different analyses when the data acquisition is not synchronized with the modulation process.

The data acquisition which not synchronized with modulation process will create a critical problem in the quantitative analysis. Because the timing of split peaks from the first dimension to the second dimension during each modulation period cannot be reproduced exactly from analysis to analysis, the relative number of peaks as well as the relative peak intensity/area of the same component may not be reproduced. The latter will affect the variation of peak volume count in GCxGC regarding which peak volume integration method is used. Table 3 shows the peak area variation when the data acquisition is synchronized with the modulation process for the C13-C16 normal paraffin standard. Both retention time and peak intensity are well reproduced. When data acquisition is not synchronized with modulation process, the number of peaks spliced within the same component as well as the relative peak intensity will vary from analysis to analysis. FIG. 4 illustrates the peak pattern of the C13-C16 normal paraffin standard for four different analyses when the data acquisition is not synchronized with the modulation process.

TABLE 3

The peak area variation when the data acquisition synchronized with modulation of C13-C16 normal paraffin standard.

|   | Retention Time | Normalized | | | | | |
|---|---|---|---|---|---|---|---|
|   |   | 1 Peak Ratio | 2 Peak Ratio | 3 Peak Ratio | 4 Peak Ratio | Average | Stdev |
| C13 | 23.391 | 4.1% | 4.0% | 4.2% | 4.7% | 4.24% | 6.67% |
|  | 23.559 | 100.0% | 100.0% | 100.0% | 100.0% | 100.00% | 0.00% |
|  | 23.723 | 6.3% | 5.6% | 6.3% | 6.4% | 6.17% | 5.86% |
| C14 | 23.391 | 2.0% | 1.9% | 1.9% | 2.0% | 1.94% | 1.32% |
|  | 23.559 | 100.0% | 100.0% | 100.0% | 100.0% | 100.00% | 0.00% |
|  | 23.723 | 50.2% | 50.1% | 52.0% | 51.4% | 50.91% | 1.80% |
| C15 | 23.391 | 2.0% | 2.0% | 2.0% | 2.1% | 2.04% | 0.94% |
|  | 23.559 | 100.0% | 100.0% | 100.0% | 100.0% | 100.00% | 0.00% |
|  | 23.723 | 66.9% | 66.0% | 68.5% | 67.9% | 67.31% | 1.62% |
| C16 | 23.391 | 5.9% | 6.0% | 6.0% | 6.1% | 5.99% | 1.42% |
|  | 23.559 | 100.0% | 100.0% | 100.0% | 100.0% | 100.00% | 0.00% |
|  | 23.723 | 22.5% | 21.1% | 22.3% | 22.3% | 22.06% | 2.95% |

EXAMPLE

The Advantages of Reproduced Chromatography in The Quantitative Analysis

Figure 5:
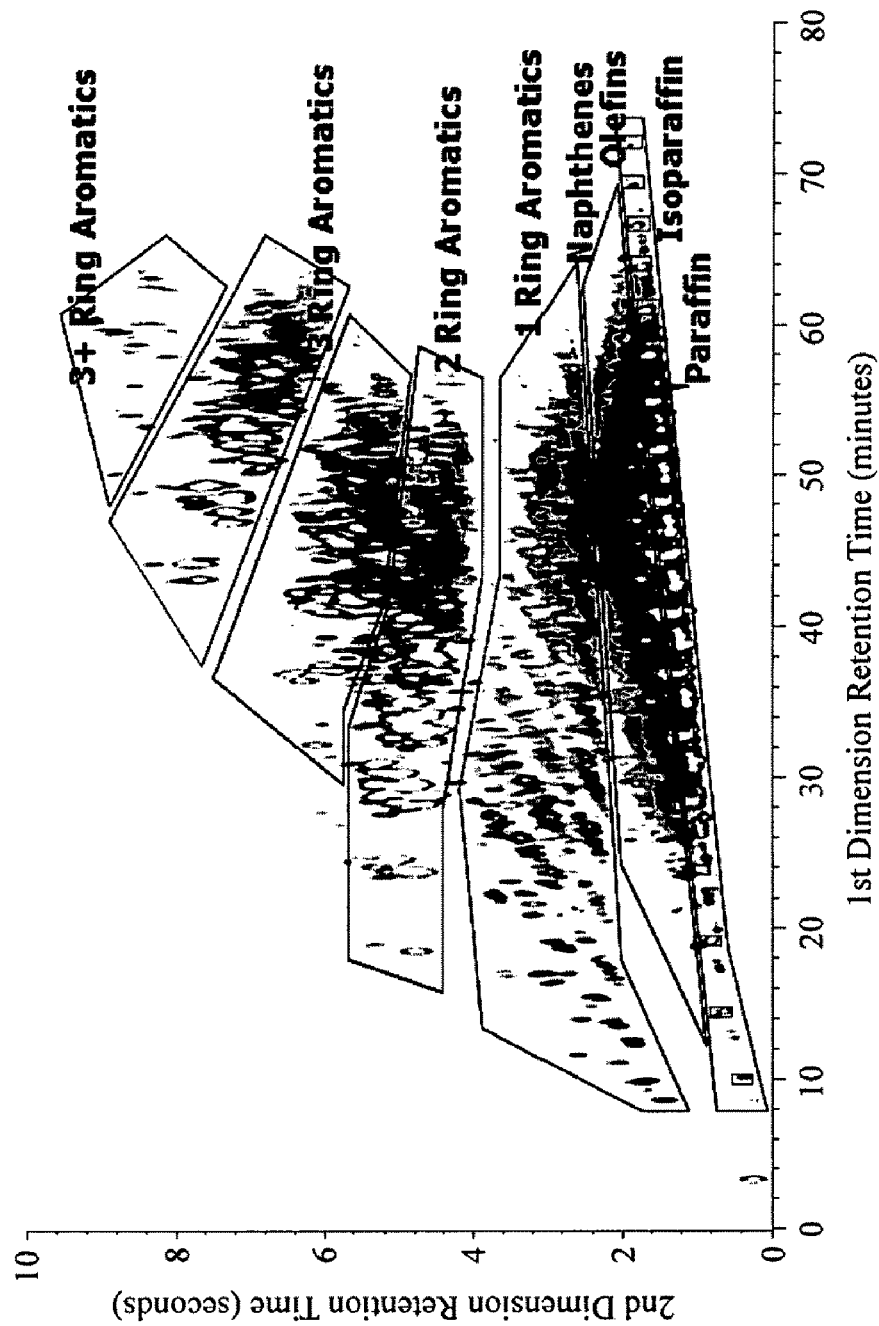
FIG. 5 shows a typical GCxGC (2DGC) chromatogram of diesel sample, various templates can be constructed for different type of quantitative analysis depending on the purpose of the experiment.

When a GCxGC (2DGC) chromatogram can be reproduced, it will make the qualitative and quantitative analysis much more effective and efficient. The component identification and quantification can be completely based on the retention position in the chromatogram and a qualitative and quantitative analysis template can be constructed for a set of samples generated in the same experimental conditions. FIG. 5 illustrates a typical GCxGC (2DGC) chromatogram of diesel sample. Various templates can be constructed for different type of quantitative analysis depend on the purpose of the experiment. The examples are given below.

Figure 6:
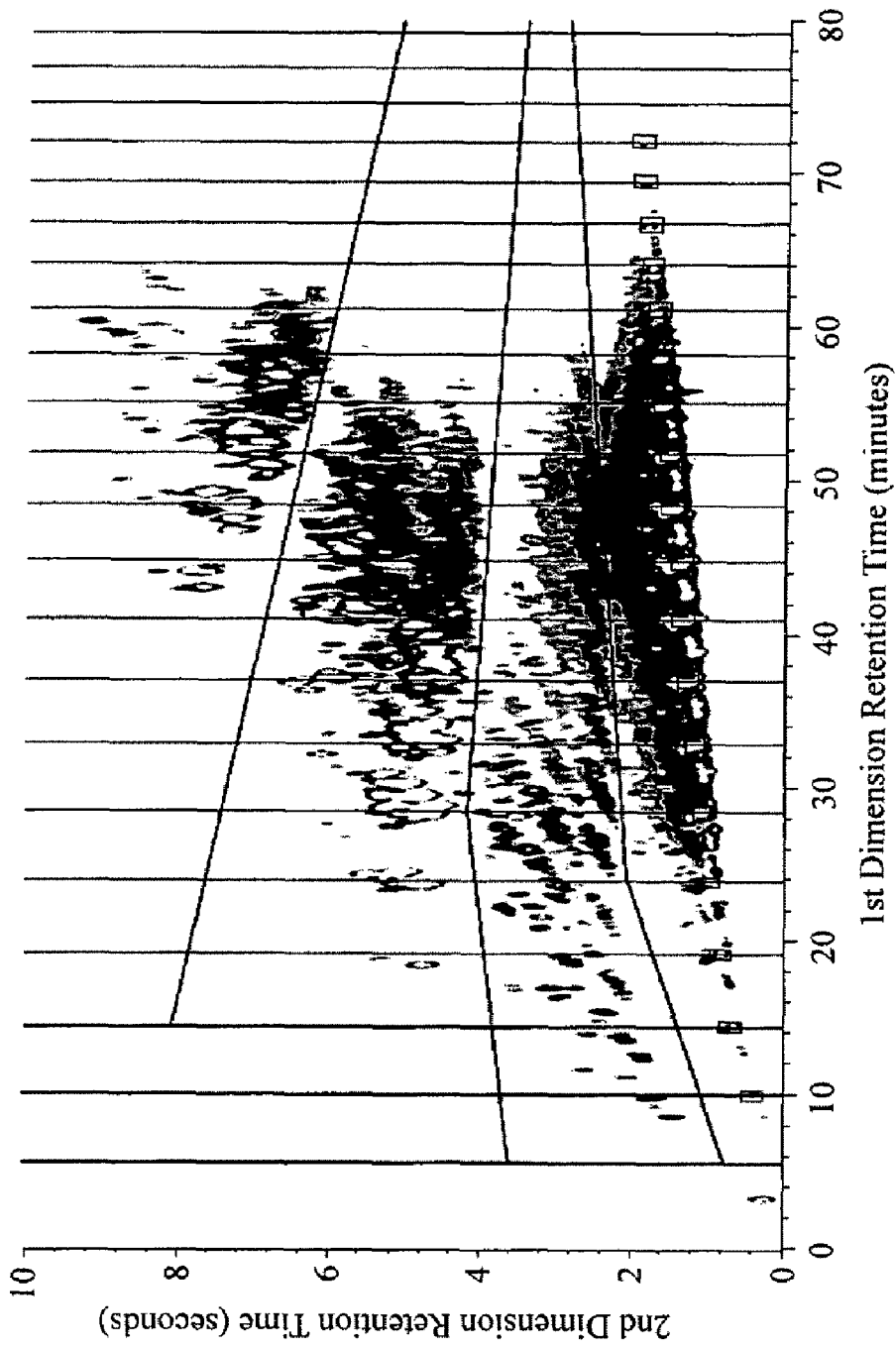
FIG. 6 shows a simulation distillation type of quantitative analysis that quantify and group each component based on its boiling point. Table 4 lists the quantitative results of this type of analysis.

FIG. 6 demonstrates a simulation distillation type of quantitative analysis that quantify and group each component based on its boiling point. Table 4 lists the quantitative results of this type of analysis.

TABLE 4

The simulation distillation type quantitative analysis results of a diesel sample.

| Temperature | Aliphatic | Arom-1R | Arom-2R | Arom-3R | Total |
|---|---|---|---|---|---|
| up to 98 | 3.20 | 0.00 | 0.00 | 0.00 | 3.20 |
| 99-126 | 4.65 | 2.24 | 0.00 | 0.00 | 6.89 |
| 127-151 | 5.05 | 2.61 | 0.00 | 0.00 | 7.65 |
| 152-174 | 6.37 | 3.32 | 0.00 | 0.00 | 9.69 |
| 175-196 | 6.81 | 3.74 | 0.00 | 0.00 | 10.55 |
| 197-216 | 5.61 | 4.34 | 0.57 | 0.00 | 10.52 |
| 217-235 | 6.92 | 3.75 | 1.44 | 0.00 | 12.10 |
| 236-254 | 7.71 | 3.24 | 1.61 | 0.00 | 12.56 |
| 255-271 | 5.67 | 2.27 | 2.66 | 0.00 | 10.60 |
| 272-287 | 3.27 | 1.33 | 1.61 | 0.00 | 6.21 |
| 288-302 | 2.82 | 0.80 | 0.84 | 0.00 | 4.46 |
| 303-316 | 1.58 | 0.41 | 0.54 | 0.04 | 2.56 |
| 317-330 | 1.04 | 0.27 | 0.31 | 0.05 | 1.67 |
| 345-356 | 0.35 | 0.14 | 0.14 | 0.06 | 0.69 |
| 357-369 | 0.17 | 0.07 | 0.06 | 0.06 | 0.35 |
| 370-380 | 0.09 | 0.04 | 0.02 | 0.02 | 0.17 |
| 381-391 | 0.04 | 0.02 | 0.01 | 0.01 | 0.09 |
| 392-402 | 0.01 | 0.01 | 0.00 | 0.01 | 0.03 |
| 403-412 | 0.00 | 0.00 | 0.00 | 0.00 | 0.00 |
| 413-422 | 0.00 | 0.00 | 0.00 | 0.00 | 0.00 |
| 423-431 | 0.00 | 0.00 | 0.00 | 0.00 | 0.00 |

TABLE 4-continued

The simulation distillation type quantitative analysis results of a diesel sample.

| Temperature | Aliphatic | Arom-1R | Arom-2R | Arom-3R | Total |
|---|---|---|---|---|---|
| 432-440 | 0.00 | 0.00 | 0.00 | 0.00 | 0.00 |
| 441-449 | 0.00 | 0.00 | 0.00 | 0.00 | 0.00 |
| Total | 61.34 | 28.59 | 9.81 | 0.26 | 100.00 |

Figure 7:
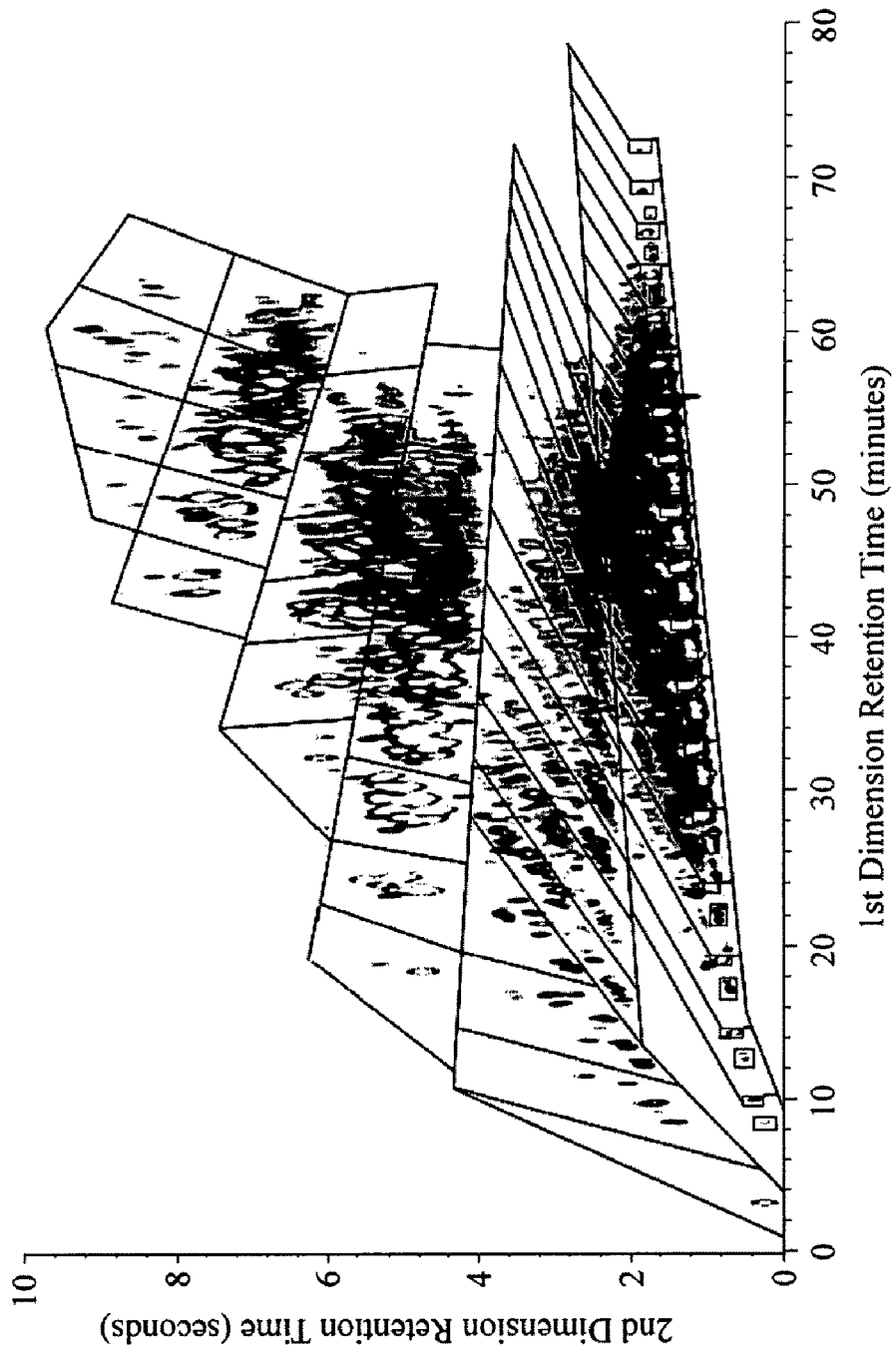
FIG. 7 shows another type of quantitative analysis based on the carbon number series that quantify and group each component based molecular structure or molecular weight. Table 5 lists the quantitative results of this type of analysis.

FIG. 7 demonstrates another type of quantitative analysis based on the carbon number series that quantify and group each component based molecular structure or molecular weight. Table 5 lists the quantitative results of this type of analysis.

TABLE 5

The carbon number series type quantitative analysis results of a diesel sample.

|  | N-Para | Iso-Para | NO | 1-Ring | 2-Ring | 3-Ring | Total |
|---|---|---|---|---|---|---|---|
| C6 |  |  |  | 1.35 |  |  | 1.35 |
| C7 | 1.08 | 1.94 | 0.19 | 0.89 |  |  | 4.10 |
| C8 | 1.12 | 4.02 | 1.87 | 2.64 |  |  | 9.65 |
| C9 | 1.03 | 1.02 | 2.56 | 4.14 |  |  | 8.76 |
| C10 | 1.24 | 1.47 | 3.83 | 4.58 | 0.51 |  | 11.63 |
| C11 | 1.36 | 1.16 | 4.22 | 3.58 | 2.17 |  | 12.49 |
| C12 | 1.22 | 1.18 | 2.89 | 4.34 | 2.56 |  | 12.20 |
| C13 | 1.29 | 1.54 | 4.36 | 2.70 | 2.07 |  | 11.96 |
| C14 | 1.43 | 1.40 | 3.87 | 1.55 | 0.92 | 0.04 | 9.21 |
| C15 | 1.07 | 1.22 | 3.49 | 1.24 | 0.46 | 0.08 | 7.56 |
| C16 | 0.73 | 0.57 | 2.05 | 0.73 | 0.30 | 0.07 | 4.46 |
| C17 | 0.80 | 0.53 | 1.32 | 0.44 | 0.20 | 0.03 | 3.31 |
| C18 | 0.37 | 0.21 | 0.84 | 0.22 | 0.11 | 0.01 | 1.75 |
| C19 | 0.13 | 0.12 | 0.41 | 0.11 | 0.06 | 0.00 | 0.82 |
| C20 | 0.06 | 0.05 | 0.22 | 0.04 | 0.03 | 0.00 | 0.41 |
| C21 | 0.03 | 0.03 | 0.10 | 0.02 | 0.02 | 0.00 | 0.21 |
| C22 | 0.01 | 0.02 | 0.04 | 0.01 | 0.01 | 0.00 | 0.09 |
| C23 | 0.00 | 0.01 | 0.03 | 0.00 | 0.00 | 0.00 | 0.04 |
| C24 | 0.00 | 0.00 | 0.01 | 0.00 | 0.00 | 0.00 | 0.01 |
| C25 | 0.00 | 0.00 | 0.00 | 0.00 | 0.00 | 0.00 | 0.00 |
| C26 | 0.00 | 0.00 | 0.00 | 0.00 | 0.00 | 0.00 | 0.00 |
| C27 | 0.00 | 0.00 | 0.00 | 0.00 | 0.00 | 0.00 | 0.00 |
| C28 | 0.00 | 0.00 | 0.00 | 0.00 | 0.00 | 0.00 | 0.00 |
| C29 | 0.00 | 0.00 | 0.00 | 0.00 | 0.00 |  | 0.00 |
| C30 | 0.00 | 0.00 | 0.00 | 0.00 | 0.00 |  | 0.00 |
| C31 | 0.00 | 0.00 | 0.00 |  |  |  | 0.00 |
| Total | 12.98 | 16.49 | 32.29 | 28.58 | 9.42 | 0.23 | 100.00 |

The invention of this synchronization unit enable the qualitative and quantitative analysis development of comprehensive two (multiple)-dimensional chromatographic separation techniques. This is the key component that bridge this comprehensive two (multiple)-dimensional chromatographic separation techniques toward the practical applications.

What is claimed is:

1. In a comprehensive two-dimensional gas chromatograph system having the elements a primary gas chromatography column, a secondary gas chromatography column that receives effluent from the primary gas chromatography column, an autosampler for injecting sample into the primary gas chromatography column, a detector for receiving effluent from the secondary chromatography column for data acquisition, a pulse generator, and a modulator having a pulse sequence for pulsing the effluent of the primary gas chromatography column to the secondary gas chromatography column, the improvement which comprises: instrument control and data acquisition software that starts the autosampler of the comprehensive two-dimensional gas chromatograph and the data acquisition by the detector and directs the autosampler to inject sample and send out a triggering signal to the pulse generator to reset the pulse sequence of the modulator thereby synchronizing the pulsing of the modulator, the start of the autosampler and data acquisition of the detector resulting in reproducible chromatograms with the same sample.

2. The system of claim 1 wherein said modulator includes a liquid nitrogen, a liquid nitrogen level control, and an automatic liquid nitrogen refill system.

3. The system of claim 1 wherein said pulse generator for synchronizing results in a retention time of less than 0.001 seconds in the secondary gas chromatography column.

4. A method to reproduce the results of a comprehensive two dimensional gas chromatography system having an autosampler, a modulator, a pulse generator and instrument control and data acquisition software wherein the improvement comprises the instrument control acquisition software sending out signals to start data acquisition by the detector, the autosampler to inject a sample and reset the modulator thereby synchronizing data acquisition with modulation.

* * * * *